United States Patent [19]

Bey et al.

[11] 4,413,141

[45] Nov. 1, 1983

[54] 2-(DIFLUOROMETHYL)-2,5-DIAMINOPENTANOIC ACID

[75] Inventors: Philippe Bey, Strasbourg; Michel Jung, Illkirch-Graffenstaden, both of France

[73] Assignee: Merrell Toraude et Compagnie, Strasbourg, France

[21] Appl. No.: 419,347

[22] Filed: Sep. 17, 1982

Related U.S. Application Data

[63] Continuation-in-part of Ser. No. 53,937, Jul. 2, 1979, abandoned, which is a continuation of Ser. No. 814,765, Jul. 11, 1977, abandoned.

[51] Int. Cl.³ .......................................... C07C 101/24
[52] U.S. Cl. .................................. 562/561; 424/319
[58] Field of Search ........................................ 562/561

[56] References Cited

U.S. PATENT DOCUMENTS

| | | | |
|---|---|---|---|
| 4,288,601 | 9/1981 | Kollonitsch et al. | 548/344 |
| 4,309,442 | 1/1982 | Bey et al. | 424/319 |
| 4,315,095 | 2/1982 | Bey et al. | 548/344 |
| 4,325,961 | 4/1982 | Kollonitsch et al. | 424/273 R |
| 4,330,559 | 5/1982 | Bey et al. | 424/319 |

*Primary Examiner*—Richard Raymond
*Attorney, Agent, or Firm*—David E. Frankhouser; Raymond A. McDonald; Gary D. Street

[57] ABSTRACT

This invention relates to 2-(difluoromethyl)-2,5-diaminopentanoic acid, or a pharmaceutically acceptable acid addition salt thereof, and to the methods for the preparation and use thereof.

3 Claims, No Drawings

2-(DIFLUOROMETHYL)-2,5-DIAMINOPENTANOIC ACID

This is a continuation-in-part of pending application Ser. No. 53,937, filed July 2, 1979, now abandoned, which is a continuation of application Ser. No. 814,765, filed July 11, 1977, now abandoned.

The present invention relates to 2-difluoromethyl-2,5-diaminopentanoic acid (DFMO), which in vitro and in vivo is an inhibitor of ornithine decarboxylase, an enzyme which is involved in polyamine formation in organisms. The invention also provides pharmaceutical compositions comprising said compounds, methods of medical treatment using said compounds, and processes for preparing said compounds.

In both eukaryotic and prokaryotic cells, the decarboxylation of ornithine to putrescine, a reaction catalyzed by ornithine decarboxylase (ODC), is the first step in the biosynthesis of the polyamines known as spermidine and spermine. Spermidine is formed by the transfer of an activated aminopropyl moiety from S-adenosyl-S-methyl homocysteamine to putrescine, while spermine is formed by the transfer of a second aminopropyl group to spermidine. Ornithine is formed from arginine by the action of arginase. S-Adenosyl-S-methyl homocysteamine is formed by the decarboxylation of S-adenosylmethionine (SAM), a reaction catalyzed by the enzyme S-adenosylmethionine decarboxylase (SAMDC). In mammals, lysine is also decarboxylated by ODC. In prokaryotic cells, lysine is decarboxylated by lysine decarboxylase.

In prokaryotic cells and in plant cells, putrescine can also be biosynthesized via an alternative pathway which involves the decarboxylation of arginine by arginine decarboxylase to yield agmatine and the conversion of agmatine to putrescine.

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis.

Since, in eukaryotic cells, putrescine is a precursor of the polyamines, spermidine and spermine, blockage of the conversion of ornithine to putrescine, such as by inhibition of ODC, will prevent new biosynthesis of these polyamines. However, the continuous synthesis of these polyamines is not vital to cell viability, provided the preexisting polyamine pool is maintained above a certain critical level. Moreover, total blockage of polyamine biosynthesis by inhibition of ODC will be difficult to maintain because of the high turnover rate of this enzyme. Nevertheless, we have found that blockage of the conversion of ornithine to putrescine according to the invention can have beneficial effects in certain cell proliferation situations, to be hereinafter discussed.

In its first composition of matter aspect, the invention sought to be patented comprehends the pharmacologically active chemical compound of the formula:

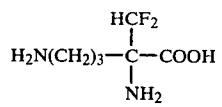

or a pharmaceutically acceptable salt thereof.

The compound represented by Formula I is 2-difluoromethyl-2,5-diaminopentanoic acid, which can also be named 2-difluoromethyl-2,5-diaminovaleric acid or α-(difluoromethyl)ornithine. The abbreviation "DFMO" is employed to refer to α-(difluoromethyl)ornithine.

Illustrative examples of pharmaceutically acceptable salts of the compound of Formula I include non-toxic acid addition salts formed with inorganic acids, such as hydrochloric, hydrobromic, sulfuric, and phosphoric acid, and organic acids, such as methane sulfonic, salicylic, maleic, malonic, tartaric, citric, cyclamic, and ascorbic acids; and non-toxic salts formed with inorganic or organic bases, such as those of alkali metals, for example, sodium, potassium, and lithium, alkaline earth metals, for example, calcium and magnesium, light metals of Group III A, for example, aluminium, organic amines, such as primary, secondary, or tertiary amines, for example, cyclohexylamine, ethylamine, pyridine, (methylamino)ethanol, ethanolamine, and piperazine. The salts are prepared by conventional means.

The compound of Formula I inhibits ornithine decarboxylase enzyme (ODC) in vitro and in vivo, and produces a decrease of putrescine and spermidine concentrations in cells in which active biosynthesis of polyamines is taking place. Therefore, the compound can be employed in specific situations to control cell growth or proliferation.

In particular, DFMO has been found to be capable of interrupting embryogenesis in female mice as described by J. Fozard, *European Journal of Pharmacology*, 65, 379 (1980). Accordingly, the compound can be used as a contragestational agent (abortifacient) in female animals when it is desired to terminate early pregnancy. The use of DFMO as a contragestational agent is described and claimed in U.S. Pat. No. 4,309,442 of P. Bey and M. Jung. In addition, DFMO has also been found to be capable of producing a significant decrease in weight of the ventral prostate in rats as described by C. Danzin et al., *Biochem. J.*, 202, 175 (1982). Accordingly, the compound can be used to treat benign prostatic hypertrophy. The use of DFMO in the treatment of benign prostatic hypertrophy is described and claimed in U.S. Pat. No. 4,330,559 of P. Bey and M. Jung.

DFMO has also been found to be capable of slowing neoplastic cell proliferation when tested in standard animal tumor models. The preferred manner of using DFMO for the treatment of neoplasms, generally, will be in conjunction with other therapeutic methods or with agents known to exhibit beneficial effects in treating neoplasms. For example, DFMO can be administered in combination with cytotoxic agents known in the art to be useful for tumor chemotherapy, such as methylglyoxal bis(guanylhydrazone), also known as MGBG. The therapy of human leukemia using DFMO in conjunction with MGBG is described by J. Jänne et al., *Med. Biol.*, 59, 448 (1981) [See also M. Simes, *Int. J. Cancer*, 28, 567 (1981)].

DFMO has also been found to be an effective antiprotozoal agent in mice against infections caused by African trypanosomes (*Trypanosoma brucei brucei, Trypanosoma brucei rhodesiense,* and *brucei gambiense*) and in chickens against infections caused by *Eimeria tenella* [See C. Bacchi et al., *Science,* 210, 332 (1980); P. McCann et al., *Med. Biol.,* 59, 434 (1981); P. McCann et al., in *Advances in Polyamine Research,* Vol. 3, edited by C. Caldarera et al., Raven Press, N.Y., 1981, pages 97–110; and H. Nathan et al., *Biochem. Pharmacol.,* 30, 3010 (1981)]. In addition, DFMO and bleomycin have been shown to exert a synergistic effect against *T. b. brucei* infections in mice [See P. Bacchi et al., *Biochem. Pharmacol.,* 31, 2833 (1982)]. Moreover, DFMO will protect mice against infections caused by the exoerythrocytic form of *plasmodium berghei,* but will not protect against infections caused by the erthrocytic form. The in vitro replication of *plasmodium falciparum* is also restricted by DFMO.

The inhibitory activity of DFMO against mammalian ODC is described by B. Metcalf et al., *J. Am. Chem. Soc.,* 100, 2551 (1978), C. Danzin et al., *Life Sciences,* 24, 519 (1979), and N. Seiler et al., *Enzyme-Activated Irreversible Inhibitors,* N. Seiler et al., Editors, Elsevier/North Holland Biomedical Press, 1978, pages 55 to 71. DFMO has been found to inhibit ODC from *Pseudomonas aeruginosa* in vitro and in intact cells. By itself, however, DFMO had no effect on cell growth. DFMO did not inhibit in vitro ODC from *Escherichia coli* or *Klebsiella pneumoniae* [See A. Kallio et al., *Biochem. J.,* 200, 69 (1981)].

The inhibition of ODC from *Trypanosoma brucei* by DFMO is described by D. Hupe et al., *Fed. Proc.* (Abstract No. 5282), 41, 1174 (1982).

Numerous publications, other than those specifically set forth herein, describing the ODC inhibitory properties of DFMO, and the end-use applications of DFMO, have appeared in the literature. All such publications, including those specifically set forth herein, are incorporated by reference into this application.

DFMO can be prepared by:

(a) treating 2,5-diaminopentanoic acid (ornithine), wherein the carboxy group and the amino group are protected, with a strong base in an aprotic solvent to form the carbanion intermediate;

(b) reacting the carbanion intermediate with a suitable difluoromethyl-halo alkylating reagent in an aprotic solvent; and (c) hydrolyzing the protected α-halomethyl ornithine compound.

The reaction sequence for the method of preparation of DFMO is shown schematically below:

SCHEME A

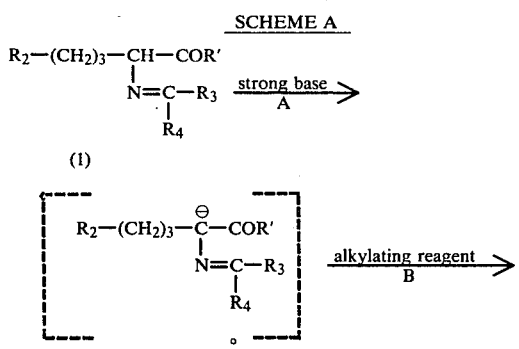

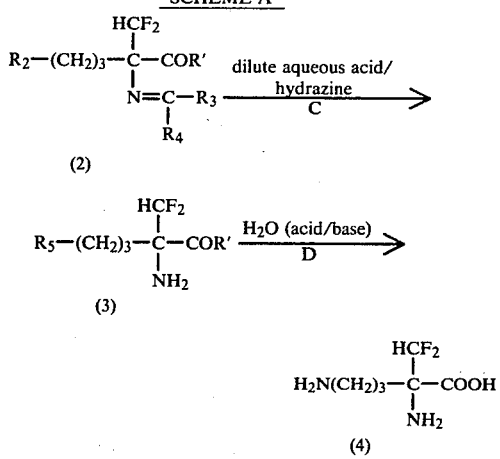

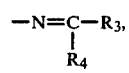

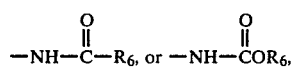

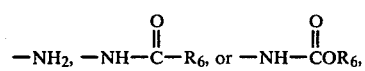

In the above reaction sequence, R' is $(C_1-C_8)$alkoxy, for example, methoxy, ethoxy, isopropoxy, n-propoxy, or tert-butoxy; $R_3$ is hydrogen, phenyl, $(C_1-C_4)$alkyl, methoxy, or ethoxy; $R_4$ is phenyl or $(C_1-C_4)$alkyl; or $R_3$ and $R_4$ taken together, may form an alkylene group of from 5 to 7 carbon atoms, that is, $-CH_2-(CH_2-)_m-CH_2-$ wherein m is an integer of from 3 to 5; $R_2$ is a group of the formula:

$$-N=C-R_3,$$
$$\quad\quad\quad |$$
$$\quad\quad\quad R_4$$

wherein $R_3$ and $R_4$ have the meanings defined above, $$-NH-\overset{O}{\overset{\|}{C}}-R_6, \text{ or } -NH-\overset{O}{\overset{\|}{C}}OR_6,$$

wherein $R_6$ is phenyl, benzyl, or $(C_1-C_4)$alkyl; $R_5$ is $$-NH_2, -NH-\overset{O}{\overset{\|}{C}}-R_6, \text{ or } -NH-\overset{O}{\overset{\|}{C}}OR_6,$$

wherein $R_6$ has the meaning defined above.

Suitable strong bases which may be employed in Step A of the above reaction sequence to form the carbanion intermediate are those which will abstract a proton from the carbon atom alpha to the carboxy group. Examples of strong bases are alkyl lithium, for example, butyl lithium or phenyl lithium; lithium di-alkylamide, for example, lithium diisopropylamide; lithium amide; sodium or potassium tert-butoxide; sodium amide; metal hydrides, for example, sodium or potassium hydride; tertiary amines, such as triethylamine; lithium acetylide or dilithium acetylide. Sodium hydride, lithium diisopropylamide, and sodium tert-butoxide are preferred bases.

Depending upon the particular base utilized, the temperature of carbanion formation can range from −100° C. to the reflux temperature of the solvent employed. In a preferred procedure, dibenzylidene ornithine ethyl ester is treated with sodium tert-butoxide in tetrahydrofuran (THF) at about 25° C. to form the corresponding carbanion.

The alkylation reaction (Step B) can be performed at a temperature of about −120° C. to 120° C., preferably about 25° to 50° C., and a reaction time of about ½ hour to 48 hours. Alkylating reagents employed in Step B of the above reaction sequence have the formula $F_2CHX$ wherein X is chlorine, bromine, or iodine. The compounds of formula $F_2CHX$ are: difluoroiodomethane, chlorodifluoromethane, or bromodifluoromethane. The alkylating reagents are known compounds.

The alkylation is carried out in a suitable aprotic solvent, such as dimethylsulfoxide, dimethylformamide, dimethylacetamide, benzene, toluene, or ethers, such as tetrahydrofuran, diethyl ether, or dioxane.

The amino or carboxy protecting groups of compound (2) can be removed to afford compound (4) in one step by treatment with an aqueous acid, for example, hydrochloric acid or toluene sulfonic acid at a temperature of about 0° to 160° C. for about 4 to 24 hours. When the amino groups are protected as a Schiff's base, it is preferred, however, to remove the amino protecting groups first by treating compound (2) with a dilute aqueous acid, for example, hydrochloric acid or with hydrazine or phenylhydrazine in a solvent, such as a lower alcohol, for example, methanol or ethanol, an ether, a chlorinated hydrocarbon, benzene, or water. Removal of the carboxylic protecting group and the amino protecting groups, when the amino groups are protected other than as a Schiff's base, can be accomplished by treatment of compound (2) with a concentrated aqueous acid, for example, hydrobromic acid at a temperature of about 0° to 160° C. or an aqueous base.

The amine and carboxy protected derivatives of formula (1), wherein $R_2$ is a group of the formula:

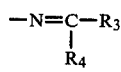

can be prepared, when $R_3$ is other than methoxy or ethoxy, by treating an ornithine ester with a suitable carbonyl compound using procedures generally known in the art for forming a Schiff's base. When R is hydrogen, the appropriate amino acid ester can be treated with benzaldehyde or a ($C_1$-$C_9$)alkanal, for example, 1-propanal, 1-butanal, 2,2-dimethylpropan-1-al, or 2,2-dimethylbutan-1-al. When $R_3$ is phenyl, the ornithine ester can be treated with benzophenone, preferably in the presence of a Lewis acid catalyst, or a phenyl ($C_1$-$C_8$)alkyl ketone, for example, phenyl methyl ketone, phenyl ethyl ketone, phenyl isopropyl ketone, phenyl n-butyl ketone, or phenyl tert-butyl ketone. When $R_3$ is ($C_1$-$C_8$)alkyl, the ornithine ester can be treated with a phenyl ($C_1$-$C_8$)alkyl ketone, as described above, or with a di-($C_1$-$C_8$)alkyl ketone, for example, dimethyl ketone, diethyl ketone, methyl isopropyl ketone, di-n-butyl ketone, or methyl tert-butyl ketone. The carbonyl compounds are known in the art, or may be prepared by procedures well known in the art.

When $R_3$ is methoxy or ethoxy, the ornithine ester can be treated with a benzoyl halide, for example, the chloride of a ($C_1$-$C_9$)alkanoic acid halide, for example, acetyl chloride, propionyl chloride, butyryl chloride, tert-butyryl chloride, 2,2-diethylbutyryl chloride, or valeryl chloride, at 0° C. in a solvent, such as an ether, methylenechloride, dimethylformamide, dimethylacetamide, or chlorobenzene, in the presence of an organic base, such as triethylamine or pyridine. The resulting amide derivative is then combined with an alkylating reagent, such as, when $R_3$ is methoxy, with methylfluorosulfonate, dimethylsulfate, methyliodide, methyl-p-toluene-sulfonate, or trimethyloxonium hexafluorophosphate, or, when $R_3$ is ethoxy, with triethyloxonium tetrafluoroborate at about 25° C. in a chlorinated hydrocarbon solvent, such as methylene chloride, chlorobenzene, or chloroform. The reaction mixture is then refluxed for about 12 to 20 hours. The mixture is then cooled to about 25° C., an aprotic base such as triethylamine or pyridine is added, the solution is quenched with brine, and the product isolated by conventional procedures.

When in compound (1), $R_3$ and $R_4$ together form ($C_5$-$C_7$)alkylene, the protected amino acid ester is obtained by treating the amino acid ester with a cyclic alkanone selected from cyclopentanone, cyclohexanone, and cycloheptanone to form a Schiff's base by procedures generally known in the art.

When $R_2$ is

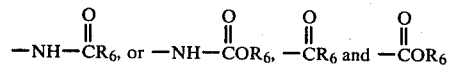

the protecting groups are introduced by the following process: The α-amino group of ornithine is protected by treating ornithine with an excess of a copper salt, for example, copper carbonate, in boiling water for about 1 to 6 hours. Upon cooling to room temperature, the mixture is filtered and the filtrate containing the copper complex is treated with an appropriate acid halide, when $R_2$ is

or an appropriate alkyl or aryl haloformate, when $R_2$ is

The acylation reaction is carried out in an inert solvent, for example, acetone, in the presence of a base, such as sodium bicarbonate or sodium hydroxide. Treatment with hydrogen sulfide then destroys the copper complex. Illustrative acid halides which may be employed are acetyl chloride, propionyl chloride, benzoyl chloride, or 2-phenylacetyl chloride. Illustrative haloformates which may be employed are benzyl chloroformate, phenyl chloroformate, methyl chloroformate, or ethyl chloroformate.

The amino acid esters employed to prepare the compounds of formula (1) can be formed by known procedures. For example, the amino acid can be treated with an appropriate alcohol, such as methanol, ethanol, or n-butanol saturated with HCl gas or, when it is desired to prepare a tert-alkyl ester, with an appropriate ($C_1$-$C_8$)alkene in the presence of a strong acid.

The method for the preparation of DFMO from ornithine methyl ester by difluoromethylation of methyl 2,5-bis(benzylideneamino)pentanoate and the deprotection of methyl 2-difluoromethyl-2,5-bis(benzylideneamino)pentanoate is described by P. Bey et al., *J. Org. Chem.*, 44, 2732 (1979), the disclosure of which is incorporated herein by reference.

DFMO can also be prepared via 2-difluoromethyl-2-amino-5-methoxypentanenitrile or 2-difluoromethyl-2- amino-5-benzyloxypentanenitrile by the method described in European Patent Application No. 0046710, published Mar. 3, 1982 (Merrell-Toraude et Compagnie).

In the reaction sequence shown hereinbefore in Scheme A, the ester compound (3) obtained in Step C can be converted, if desired, to the corresponding lactam which can then be hydrolyzed to give the desired product (4). The hydrolysis can be performed using methods generally known in the art. For example, the lactam can be treated with 6 N hydrochloric acid at reflux temperature for 24 hours.

The lactam of DFMO, which is 3-difluoromethyl-3-amino-2-piperidone, can be made by treating a ($C_1$–$C_8$)alkyl ester of DFMO as an acid addition salt with a base (such as sodium hydroxide, potassium hydroxide, lithium hydroxide, sodium carbonate, potassium carbonate, sodium methoxide, potassium tert-butoxide, sodium amide, or an organic amine, e.g. trialkylamine, such as triethylamine) in a solvent (such as a lower alkanol, e.g. methanol, ethanol, isopropyl alcohol, n-butanol, water, dimethylformamide, dimethylsulfoxide, hexamethylphosphoramide) using a temperature of 0° to 120° C. and a reaction time of ½ hour to 24 hours.

In general, the ($C_1$–$C_8$)alkyl esters of DFMO can be prepared directly from 2-difluoromethyl-2,5-diaminopentanoic acid using conventional esterification methods, such as:

(a) treatment with an appropriate alcohol (R′—OH) saturated with hydrogen chloride using a reaction time of about 1 to 7 days at a temperature of about 25° C. to the boiling point of the alcohol employed, or (b) formation of the corresponding acid halide from the amino acid, preferably the acid chloride, by treatment with thionyl chloride, followed by alcoholysis using the corresponding alcohol (R′—OH).

Alternatively, in a preferred method, certain esters can be prepared by treating a salt of an amine-protected DFMO, such as the dicyclohexylammonium salt, with an alkyl-halo compound of the formula R′—X in the presence of sodium iodide, when X is other than iodo, and then removing the amine protecting groups. In formula R′—X, R′ is ($C_1$–$C_8$)alkyl and X is chlorine, bromine, or iodine, with the proviso that the alkyl group may not have a tertiary carbon atom present at the carbon-halogen bond. The esterification reaction is preferably performed in dimethylformamide at room temperature for 24 hours. The preferred amine-protecting group is tert-butyloxycarbonyl, since the group can be removed under acidic conditions.

When it is desired to prepare a tert-alkyl ester of DFMO, an appropriate amine-protected DFMO can be reacted with an appropriate tert-alkyl acetate and perchloric acid, and the amine-protecting group can then be removed under conditions that do not affect the tert-alkyl ester group. For example, the t-butyl ester of DFMO can be prepared from 5-N-benzyloxycarbonyl-2-difluoromethyl-2,5-diaminopentanoic acid by reaction with t-butyl acetate and perchloric acid at room temperature followed by hydrogenation at 1 atmosphere with Pd/C in ethanol at room temperature.

The methyl ester of DFMO can be prepared conveniently by treating 2,5-N-tert-butyloxycarbonyl-2-difluoromethyl-2,5-diaminopentanoic acid, with diazomethane, followed by removal of the protecting groups.

The ($C_1$–$C_8$)alkyl esters of DFMO can also be obtained by deprotection of the appropriate ($C_1$–$C_8$)alkyl 2-(difluoromethyl)-2,5-bis(benzylideneamino)pentanoate under mild conditions whereby the benzylidene groups are selectively removed. This can be accomplished using mild acidic conditions [1 N hydrochloric acid, room temperature, as described by P. Bey et al., J Org. Chem., 44, 2732 (1979)] or using the reaction with hydrazine. The use of hydrazine is preferred for compounds having a tertiary-alkyl ester group, since the tert-alkyl ester function will undergo hydrolysis under acidic conditions.

In general, the esters of DFMO must be in the form of an acid addition salt in order to prevent or minimize lactam formation.

It will be apparent to those skilled in the art that DFMO contains a chiral center, and that, therefore, the compound can exist in the form of an individual optical isomer (enantiomer) or of mixtures thereof, such as the racemate. Methods of resolving racemic DFMO are known in the art. For example, (+)-and (−)-DFMO as the monohydrochloride can be obtained as described by P. Bey et al., J. Org. Chem., 44, 2732 (1979) via resolution of DL-3-amino-3-difluoromethyl-2-piperidone with enantiomeric binaphthylphosphoric acid using the procedure of J. Jacques et al., Tetrahedron Letters, 48, 4617 (1971) followed by hydrolysis of the individual lactam isomers. The ODC inhibitory activity of DFMO resides only with the (−)-isomer [(see B. Metcalf et al., J. Am. Chem. Soc., 100, 2552 (1978)].

As employed herein and in the claims, the term "(−)-isomer" refers to the individual optical isomer (enantiomer) of DFMO which, in the form of the monohydrochloride acid addition salt, exhibits a levorotatory specific rotation (methanol).

As a pharmaceutical agent, DFMO can be administered in various manners to achieve the desired effect. The compound can be administered alone or in combination with pharmaceutically acceptable carriers or diluents, the proportion and nature of which are determined by the solubility and chemical properties of the compound selected, the chosen route of administration, and standard pharmaceutical practice. The compound may be administered orally in solid dosage forms, e.g. capsules, tablets, powders, or in liquid forms, e.g. solutions or suspensions. The compound may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stabilizing, solubilizing, or suspending agents. Parenteral preparations are sterile aqueous or non-aqueous solutions or suspensions which may contain various preserving, stabilizing, buffering, solubilizing, or suspending agents. If desired, additives, such as saline or glucose, may be added to make the solutions isotonic.

The amount of effective compound administered will vary and can be any effective amount. Depending on the patient to be treated, the condition being treated, the mode of administration, and the particular compound employed, the effective amount of DFMO administered will vary from about 0.1 mg/kg to 500 mg/kg of body weight of the patient per unit dose. Preferably the dose is between 2 to 12 g/day/70 kg body weight, preferably given by water solutions suitable for oral administration.

As used herein, the term "patient" is taken to mean warm blooded animals such as mammals, for example, cats, dogs, rats, mice, guinea pigs, horses, bovine cows, sheep, and humans.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

The invention also provides pharmaceutical formulations in which form the active compound of the invention will normally be utilized. Such formulations are prepared in a manner well known in the pharmaceutical art and usually comprise at least one active compound of the invention and a pharmaceutically acceptable carrier or diluent therefor. A carrier or diluent may be solid, semisolid, or liquid material which serves as a vehicle, excipient, or medium for the active ingredient. Suitable diluents or carriers are well known. The pharmaceutical formulations may be adapted for enteral or parenteral use and may be administered to the patient in the form of tablets, capsules, suppositories, solutions, suspensions, or the like.

The following examples illustrate the methods and procedures for making and using DFMO. Except as otherwise indicated, melting point determinations were made using a Kofler hot bank apparatus.

EXAMPLE 1

($\pm$)-3-Amino-3-difluoromethyl-2-piperidone

To a solution of ($\pm$)-methyl 2-difluoromethyl-2,5-diaminopentanoate dihydrochloride (2.7 g) in dry methanol (30 ml) is added under nitrogen 2 equivalents of sodium methylate in methanol (0.46 g of sodium in 20 ml of methanol). The reaction mixture is stirred for 3 hours at room temperature, then the solvent is evaporated under reduced pressure. The residue is extracted with ether to yield crude ($\pm$)-3-amino-3-difluoromethyl-2-piperidone which is purified either by crystallization from CHCl$_3$/pentane (m.p. 149° C.) or by distillation (b.p. 135° C./0.05 mm Hg).

EXAMPLE 2

A. ($-$)- and ($+$)-2-Amino-3-difluoromethyl-2-piperidone hydrochloride

To a solution of ($-$)-binaphthylphosphoric acid (BNPA) (1.27 g) in hot ethanol (50 ml) is added a solution of ($\pm$)-3-amino-3-difluoromethyl-2-piperidone (0.546 mg) in hot ethanol (5 ml). On cooling, crystals separate. The reaction mixture is then left stand at 4° C. overnight. The precipitate is filtered and washed with ethanol and diethyl ether to give 0.54 g of the ($-$)-binaphthylphosphoric salt: [$\alpha$]$_D$= $-409°$ (C=0.3, MeOH); m.p. 300° C. Recrystallization of the mother liquor yields 0.15 g of ($-$)-binaphthylphosphoric salt. Concentration of the filtrate gives 1.1 g of a sticky material which is treated with HCl 3 M at room temperature for 3 hours. The ($-$)-BNPA is filtered and the filtrate concentrated under reduced pressure. Recrystallization of the residue (320 mg) in ethanol affords ($+$)-3-amino-3-difluoromethyl-2-piperidone as the monohydrochloride, (160 mg): [$\alpha$]$_D$= $+18°6$ (C=1; MeOH); m.p. 238° C. Treated in the same condition,, the ($-$)-BNPA salt (436 mg) gives ($-$)-3-amino-3-difluoromethyl-2-piperidone as the monohydrochloride (137 mg) which is recrystallized in ethanol (67 mg): [$\alpha$]$_D$= $-19°$ (C=1.02, MeOH); m.p. 240° C. dec.

B. ($-$)- and ($+$)-2-Difluoromethyl-2,5-diaminopentanoic acid, monohydrochloride ($-$)-3-Difluoromethyl-3-amino-2-piperidone hydrochloride (60 mg) is heated in HCl 6 M (4 ml) at reflux for 12 hours. After concentration under reduced pressure, the residue is dissolved in water and the pH of the solution is adjusted to 4.5 with a solution of NEt$_3$. The solution is then concentrated under reduced pressure and the residue extracted many times with chloroform and then recrystallized from H$_2$O/EtOH to give ($+$)-2-difluoromethyl-2,5-diaminopentanoic acid monohydrochloride (54 mg): [$\alpha$]$_D$= $+6°$ (C=0.48, MeOH); m.p. $\geq 240°$ C.). By an identical treatment, ($+$)-3-difluoromethyl-3-amino-2-piperidone as the hydrochloride (96 mg) gives ($-$)-2-difluoromethyl-2,5-diaminopentanoic acid as the monohydrochloride (56 mg): [$\alpha$]$_D$= $-10°$ (C=0.7, MeOH); m.p. $\geq 244°$ C.

EXAMPLE 3

2-Difluoromethyl-2,5-diaminopentanoic acid

Under nitrogen, a solution (500 ml) of 2 M butyllithium in hexane is added to a stirred solution of diisopropylamine (143.1 ml) in tetrahydrofuran (1.5 l) at $-78°$ C. after which dibenzylidene ornithine methyl ester (261 g, 0.81 mole) in tetrahydrofuran (1.5 l) is added. Upon completion of the addition, the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l) for 3 hours, the mixture extracted several times with chloroform and the aqueous solution evaporated to dryness. The oily residue is refluxed with 12 N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with acetone (7–8 l). The precipitated product is filtered off and washed with ethanol. The crude product is recrystallized by dissolving in hot water (about 150 ml) and treatment of the solution with hot ethanol (450 ml). On cooling crystals of 2-difluoromethyl-2,5-diaminopentanoic acid as the hydrochloride monohydrate separate (71 g): m.p. 183° C.

EXAMPLE 4

Dibenzylidene ornithine ethyl ester

A one liter reaction flask is charged with ornithine ethyl ester dihydrochloride (93.29 g) and methylene chloride (200 ml). The suspension is stirred and cooled to 0° C. The reactor is then charged with a solution of benzaldehyde (86 g) in methylene chloride (200 ml). The temperature is maintained at 0° C., and a solution of triethylamine (90 g) in methylene chloride (140 ml) is added during one hour. The mixture is stirred overnight at room temperature. Water (150 ml) is added, and after decantation, the organic layer is washed with water (3×150 ml) and brine (2×100 ml). The organic layer is dried over sodium sulfate (50 g). After filtration, the solvent is evaporated under reduced pressure. The oily residue obtained is well stirred with hexane (600 ml) during one hour at room temperature. After filtration and drying under reduced pressure, dibenzylidine ornithine ethyl ester is obtained as a white solid, m.p. 41.4° C.; assay: 97.33%.

EXAMPLE 5

2-Difluoromethyl-2,5-diaminopentanoic acid

A one liter reaction flask under nitrogen is charged with sodium tert-butoxide (40 g) and dried tetrahydrofuran (400 ml). The mixture is stirred at 25° C. and a solution of dibenzylidene ornithine ethyl ester (95%) (67.28 g), prepared as in Example 4, in dried tetrahydrofura (200 ml) is added quickly (10 minutes). At the end of the addition, a rapid stream of chlorodifluoromethane is bubbled through the solution. The temperature rises to 50° C. The stirring is continued under chlorodifluoromethane at 45°–50° C. for one hour. The mixture is evaporated under reduced pressure and the residue is stirred with methylene chloride (280 ml). The insoluble material is removed by filtration and the organic layer is washed with water (4×70 ml) and dried over sodium sulfate (50 g). After filtration and evaporation of the solvent under reduced pressure, crude dibenzylidene α-difluoromethylornithine ethyl ester (71.1 g) is obtained as a brown oil. This crude product is stirred at room temperature for three hours with HCl 1 N (400 ml). Then, the aqueous layer is washed with chloroform (3×100 ml). The aqueous layer is refluxed overnight with HCl 10 N (400 ml). After cooling, the solution is washed with chloroform (3×100 ml) and evaporated to dryness under reduced pressure. The residue obtained (49.68 g) is dissolved in water (80 ml), triethylamine (~25 ml) is added until a pH of 3.5 is obtained. Charcoal (0.5 g) is added and the mixture is heated for two hours to 60°–70° C. The mixture is filtered and ethanol (320 ml) is added to the filtrate. After stirring for one hour at +5° C., the crystals are filtered and dried. Crude 2-difluoromethyl-2,5-diaminopentanoic acid is obtained. The crude material is dissolved in water (30 ml), then charcoal (0.5 g) is added, and the mixture is stirred at 60°–70° C. during 20 minutes. After filtration, ethanol (120 ml) is added to the filtrate, and the mixture is stirred for one hour at 5° C. The crystals are filtered and dried to obtain 2-difluoromethyl-2,5-diaminopentanoic acid, as the hydrochloride monohydrate, m.p. 225.1°–226.4° C. (USP capillary tube method for Class Ia compounds).

For administering DFMO clinically, oral liquid formulations are preferred. Illustrative oral liquid formulations are given in the following examles:

EXAMPLE 6

DFMO Reconstitutable dry "beverage" base

| Material | Amount (g)/Unit dose |
|---|---|
| Fries & Fries Grapefruit Flavoring #91470 | 0.50 |
| Fructose, USP | 3.00 |
| Aspartame | 0.05 |
| Citric acid, anhydrous | 0.20 |
| DFMO | 3.00 |

The above formulation is reconstitutable with water to give 200 ml of solution.

EXAMPLE 7

DFMO Oral solution

| Material | per 15 ml |
|---|---|
| DFMO | 3.00 g |
| Alcohol | 0.75 ml |
| Sodium benzoate | 15.00 mg |
| Glycerin | 0.75 ml |
| Propylene glycol | 1.50 ml |
| Saccharin sodium | 18.00 mg |
| Sodium citrate | — |
| Citric acid | — |
| Sodium chloride | — |
| Purified water | q.s. 15 ml |

Add the sodium benzoate and saccharin to a portion of distilled water, heat to 50°–60° C., add the DFMO, and dissolve. Cool solution to 25°–30° C. and sequentially add and mix the alcohol, glycerin, and propylene glycol. Add water to volume, mix, and filter.

EXAMPLE 8

When DFMO is administered in large doses (up to 15 g/day70 kg body weight), it is convenient to prepare pre-measured 1, 2½, and 5 g packets of granulated DFMO which are added to appropriate amounts of water (100–300 ml) for immediate ingestion.

What is claimed is:

1. 2-Difluoromethyl-2,5-diaminopentanoic acid, or a pharmaceutically acceptable salt thereof.

2. A compound as defined in claim 1 which is the (−)-isomer of 2-difluoromethyl-2,5-diaminopentanoic acid or a pharmaceutically acceptable salt thereof.

3. The compound of claim 1 or 2 which is the monohydrochloride salt.

* * * * *